United States Patent
Wang et al.

(10) Patent No.: US 8,802,882 B2
(45) Date of Patent: Aug. 12, 2014

(54) COMPOSITION AND METHOD FOR LOW TEMPERATURE CHEMICAL VAPOR DEPOSITION OF SILICON-CONTAINING FILMS INCLUDING SILICON CARBONITRIDE AND SILICON OXYCARBONITRIDE FILMS

(75) Inventors: Ziyun Wang, Bethel, CT (US); Chongying Xu, New Milford, CT (US); Bryan C. Hendrix, Danbury, CT (US); Jeffrey F. Roeder, Brookfield, CT (US); Tianniu Chen, Rocky Hill, CT (US); Thomas H. Baum, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 12/862,739

(22) Filed: Aug. 24, 2010

(65) Prior Publication Data

US 2010/0314590 A1 Dec. 16, 2010

Related U.S. Application Data

(63) Continuation of application No. 12/578,262, filed on Oct. 13, 2009, now Pat. No. 7,781,605, which is a continuation of application No. 10/870,106, filed on Jun. 17, 2004, now Pat. No. 7,601,860, which is a continuation-in-part of application No. 10/683,501, filed on Oct. 10, 2003, now Pat. No. 7,579,496.

(51) Int. Cl.
*C07F 7/10* (2006.01)

(52) U.S. Cl.
CPC ........................................ *C07F 7/10* (2013.01)
USPC .......................................... 556/410; 514/63

(58) Field of Classification Search
CPC ........................................................ C07C 7/10
USPC .............................................. 514/63; 556/410
See application file for complete search history.

(56) References Cited

U.S. PATENT DOCUMENTS

| | | | |
|---|---|---|---|
| 5,204,141 A | 4/1993 | Roberts et al. | |
| 5,424,095 A | 6/1995 | Clark et al. | |
| 5,744,196 A | 4/1998 | Laxman et al. | |
| 5,990,541 A | 11/1999 | Saito | |
| 6,383,955 B1 | 5/2002 | Matsuki et al. | |
| 6,410,463 B1 | 6/2002 | Matsuki | |
| 6,936,548 B2 | 8/2005 | Dussarrat et al. | |
| 7,019,159 B2 | 3/2006 | Dussarrat et al. | |
| 7,064,083 B2 | 6/2006 | Dussarrat et al. | |
| 7,531,679 B2 | 5/2009 | Wang et al. | |
| 7,579,496 B2 | 8/2009 | Wang et al. | |
| 7,601,860 B2 | 10/2009 | Wang et al. | |
| 7,713,346 B2 | 5/2010 | Wang et al. | |
| 7,781,605 B2 | 8/2010 | Wang et al. | |
| 7,863,203 B2 | 1/2011 | Wang et al. | |
| 8,242,032 B2 | 8/2012 | Wang et al. | |
| 2001/0048973 A1 | 12/2001 | Sato et al. | |
| 2003/0129826 A1 | 7/2003 | Werkhoven et al. | |
| 2004/0121085 A1 | 6/2004 | Wang et al. | |
| 2004/0138489 A1 | 7/2004 | Wang et al. | |
| 2004/0146644 A1 | 7/2004 | Xiao et al. | |
| 2005/0009320 A1 | 1/2005 | Goundar | |
| 2008/0160174 A1 | 7/2008 | Wang et al. | |
| 2009/0281344 A1 | 11/2009 | Wang et al. | |

FOREIGN PATENT DOCUMENTS

EP 1 441 042 A1 7/2004
JP 2000-080476 A 3/2000

OTHER PUBLICATIONS

Smirnova, T.P., et al., "Composition and Structure of films deposited from silyl derivatives of assymetric dimthyl hydrazines.", "Inorg. Mat.", 2003, pp. 117-122, vol. 39, No. 2.
Sergeeva, Z. I. et al., "Synthesis of alkyl- and dialkylbis(1,1-dialkylhydrazino)silanes (CAPLUS Abstract)", "Zhurnal Obshceii Khimii", 1960, pp. 694-695, vol. 30, Abstract Only: Chem. Abstracts Accession No. 1960:127948.
Sergeeva, et al., "Synthesis of 1,1-dialkyl-2-(trialkylsilyl)hydrazines (CAPLUS Abstract)", "Khim. i Prakt. Primenenie Kremneorg. Soedinenii", 1958, pp. 235-241, No. 1, Abstract Only: Chem. Abstracts Accession No. 1959:62140.
Chen, L.C., et al., "Crystalline silicon carbon nitride: A wide band gap semiconductor", "Appl. Phys. Letters.", May 11, 1998, pp. 2463-2465, vol. 72, No. 19.
Witte-Abel, Henning, et al., "Kondensationen von Silylhydrazinen und Estern zu Silylhydrazonen und Pyrazolnen", "J. Organometallic Chem.", Aug. 15, 1999, pp. 341-347, vol. 585, No. 2 (English Language Abstract Provided).
Denk, Michael, et al., "Synthesis and Structure of a Stable Silylene", "J. Am. Chem. Soc.", Mar. 23, 1994, pp. 2691-2692, vol. 116, No. 6.
Gibson, George, et al., "The Reaction of Silicon Tetrachloride with N,N-Dimethylhydrazine and Hydrazine", "Inorg. Chem.", Aug. 1963, pp. 876-878, vol. 2, No. 4.
Lee, Gyun-Hwan, et al., "Bis[bis(trimethylsilyl)amino]silylene, an Unstable Divalent Silicon Compound", "J. Am. Chem. Soc.", Jul. 9, 2003, pp. 8114-8115, vol. 125, No. 27.
Mitzel, Morbert W., "Simple silylhydrazines as models for Si—N beta-donor interactions in SiNN units", "Chem. Eur. J.", 1998, pp. 692-698, vol. 4, No. 4.
Scherer, Otto, et al., "Ethylenimine and imidazolidinone derivatives of silicon(CAPLUS Abstract)", "Chem. Berichte", 1965 vol. 98, No. 7, Abstract Only, Chem. Abstracts Accession No. 1965:439205.
Sergeeva, Z.I., et al., "A new method of synthesis of organosilicon hydrazines (CAPLUS Abstract)", "Zhurnal Obshchei Khimii", 1962, pp. 1987-1993, vol. 32, Abstract Only, Chem. Abstracts Accession No. 1963:27415.
Sergeeva, Z. I., et al., "Reaction of nonsymmetric dialkylhydrazines with alkylchloro-silanes (Caplus Abstract)", "Zhurnal Obshchei Khimii", 1963, pp. 1874-1878, vol. 33, Abstract Only, Chem. Abstracts Accession No. 1963:455161.

(Continued)

*Primary Examiner* — Elvis O Price
(74) *Attorney, Agent, or Firm* — Hultquist, PLLC; Steven J. Hultquist; Maggie Chappuis

(57) ABSTRACT

Silicon precursors for forming silicon-containing films in the manufacture of semiconductor devices, such as films including silicon carbonitride, silicon oxycarbonitride, and silicon nitride ($Si_3N_4$), and a method of depositing the silicon precursors on substrates using low temperature (e.g., <550° C.) chemical vapor deposition processes, for fabrication of ULSI devices and device structures.

20 Claims, 1 Drawing Sheet

(56) References Cited

OTHER PUBLICATIONS

Smirnova, T.P., et al., "Plasma-enhanced chemical vapor deposition of silicon carbonitride films from volatile silyl derivatives of . . . ", "Proceedings of the 3rd Symposium on Theoretical and Applied Plasma Chemistry, High Energy Chemistry", 2003, pp. 303-309, vol. 37, No. 5.

Smirnova, T.P., et al., "SiCN alloys obtained by remote plasma chemical vapour deposition from novel precursors", "Thin Solid Films", Apr. 1, 2003, pp. 144-151, vol. 429, No. 1-2.

West, Robert, et al., "Chemical Shift Tensors and NICS Calculations for Stable Silylenes", "J. Am. Chem. Soc.", Feb. 25, 1998, pp. 1639-1640, vol. 120, No. 7.

"Wikipedia Entry for the term 'Vapor Pressure'", "Found online at http://en.wikipedia.org/wiki/Vapor_pressure", Jul. 17, 2007.

West, Robert, et al., "Stable silylenes: Synthesis, structure, reactions", "Pure & Appl. Chem.", 1996, pp. 785-788, vol. 68, No. 4.

Voronkov, et al., "Izvestiya Vysshikh Uchebnykh Zavedenii", "Materialy Elektronnoi Tekhniki", 2002, pp. 57-60, vol. 4 (Machine Translation of Abstract Only).

Wannagat, Ulrich, et al., "Abstract of 'Hydrazine-silicon compounds II Mixed alkyl-or aryl-substituted hydrazines'", "Z. anorg. u allgem. Chem.", 1959, pp. 341-348, vol. 299; Abstract Only, Chem. Abstracts Accession No. 1959:93473.

Wannagat, U., et al., "'Si—N compounds. L-III. Si—N2H4 compounds. 7. Some new hyrdazinosilanes'", "Monatshefte fuer Chemie", 1965, pp. 1902-1908, vol. 96, No. 6, Abstract Only, Chem. Abstracts Accession No. 1966:104351.

Wannagat, U., et al., "Silicon-Nitrogen compounds. LXI. Silicaonhydrazine compounds. 11. Hypergolity of silyhydrazi", "Monatshefte fuer Chemie", 1966, pp. 1157-1162, vol. 97, No. 4, Abstract Only, Chem. Abstracts Accession No. 1966:18737.

West, Robert, et al., "Tetramesityldisilene, a Stable Compound Containing a Silicon-Silicon Double Bond", "Science", Dec. 18, 1981, pp. 1343-1344, vol. 214, No. 4527.

Co-pending U.S. Appl. No. 12/838,441.

Co-pending U.S. Appl. No. 12/777,519.

NOTE: As to any co-pending U.S. applications cited herein, Applicant will provide at the examiner's request copies of any documents desired by the examiner from the USPTO file history of any such co-pending applications.

Rakhlin, V., et al., "Organosilicon Derivatives of 1,1-Dimethylhydrazine: Novel Precursors of Thin-Film Dielectric Coatings", "Doklady Chemistry", Feb. 2003, pp. 47-49, vol. 388, No. 4-6.

Smirnova, T., et al., "Microstructure and Chemical Bonding in Silicon Carbonitride Films Synthesized by Plasma Enhanced Chemical Vapor Deposition", "Journal of Structural Chemistry", Jan. 2003, pp. 169-173, vol. 44, No. 1.

Haaf, M., et al., "Synthesis and Reactivity of the Stable Silylene N,N'-Di-Tert-Butyl-1,3-Diaza-2-Sila-2-Ylidene", "Canadian Journal of Chemistry", Nov. 2000, pp. 1526-1533 (Abstract), vol. 78, No. 11.

COMPOSITION AND METHOD FOR LOW TEMPERATURE CHEMICAL VAPOR DEPOSITION OF SILICON-CONTAINING FILMS INCLUDING SILICON CARBONITRIDE AND SILICON OXYCARBONITRIDE FILMS

CROSS REFERENCE TO RELATED APPLICATIONS

This application is a continuation under 35 USC 120 of U.S. patent application Ser. No. 12/578,262, filed on Oct. 13, 2009, issued as U.S. Pat. No. 7,781,605 on Aug. 24, 2010, which is a continuation under 35 USC 120 of U.S. patent application Ser. No. 10/870,106 entitled "Composition and Method for Low Temperature Chemical Vapor Deposition of the Silicon-Containing Films Including Silicon Carbonitride and Silicon Oxycarbonitride Films," filed on Jun. 17, 2004 in the names of Ziyun Wang, Chongying Xu, Bryan Hendrix, Jeffrey Roeder, Tianniu Chen and Thomas H. Baum, issued Oct. 13, 2009 as U.S. Pat. No. 7,601,860, which in turn is a continuation-in-part under 35 USC 120 of U.S. patent application Ser. No. 10/683,501 entitled "Monosilane or Disilane Derivatives and Method for Low Temperature Deposition of Silicon-Containing Films Using the Same," filed on Oct. 10, 2003 in the names of Ziyun Wang, Chongying Xu and Thomas H. Baum, and issued Aug. 25, 2009 as U.S. Pat. No. 7,579,496.

FIELD OF THE INVENTION

The present invention relates generally to novel silicon-containing precursors and the formation of silicon-containing films using said precursors in the manufacture of semiconductor devices. More specifically, the present invention relates to silicon-containing precursors and methods for forming silicon-containing films, e.g., films including silicon carbonitride and silicon oxycarbonitride, on a substrate using low temperature (T<550° C.) chemical vapor deposition (CVD) processes.

DESCRIPTION OF THE RELATED ART

In semiconductor manufacturing, thin (e.g., <1,000 nanometers thickness) passive layers of chemically inert dielectric materials, such as silicon nitride ($Si_3N_4$), silicon-oxynitride ($SiO_xN_y$) and/or silicon dioxide ($SiO_2$), are widely employed in microelectronic device structures, to function as structural elements of the multi-layered structure, such as sidewall spacer elements, diffusion masks, oxidation barriers, trench isolation coatings, inter-metallic dielectric materials, passivation layers and etch-stop layers.

Recently studies have shown that carbon incorporation (10-15%) in silicon nitride films is beneficial to film quality for transistor sidewall spacer applications. Etch stop and capping layers situated between low dielectric constant (low-k) layers also benefit from a mixture of carbon with silicon nitride or silicon oxide. In addition, pre-metal dielectric (PMD)-liners of silicon nitride require etch selectivity and diffusion barrier properties, which can be enhanced by carbon incorporation into the silicon nitride.

Silicon carbonitride (Si—C—N), which displays the properties of silicon nitride and silicon carbide, is both temperature and oxidation resistant. As such, Si—C—N material is being investigated for use as a hard mask, etch stop or a passivation layer for the Cu dual damascene process.

Si—C—N layers are generally grown using various plasma-enhanced chemical deposition techniques (PECVD).

Deposition of silicon-containing films by CVD techniques is a highly attractive methodology for forming such Si—C—N films. Towards that end, mixtures of monosilane, hydrocarbons, and ammonia or nitrogen have generally been used to synthesize Si—C—N films using CVD at elevated temperatures (T~1300 K). For example, crystalline thin films of Si—C—N have been grown by microwave plasma enhanced CVD (PECVD) at temperatures above 800° C. using a mixture of $H_2$, $CH_4$, $N_2$ and $SiH_4$ gases. However, these mixtures tend to be explosive and flammable. (see, Chen, L. C., et al., *Applied Physics Letters*, 72, 2463-2465 (1998)). More recently, Si—C—N films have been deposited using PECVD at 350° C. to 400° C. using a mixture of trimethylsilane (3MS), helium and ammonia (see, Foresight, April 2003, publication of Applied Materials Taiwan). This disclosed deposition requires high plasma densities that can damage device structures if used in the "front end," e.g., the PMD-liner.

To be compatible with the next generation IC device manufacturing, sidewall spacers need to be deposited by thermal CVD processes at low deposition temperatures, e.g., temperatures less than about 550° C., preferably about 530° C. Because of stringent conformality requirements and proximity to the transistor channel, the use of plasmas is not permitted. Presently used precursors, such as BTBAS, require very high precursor flow rates and have extremely low deposition rates at these temperatures, leading to very high processing costs. Thus, there is a significant need for suitable precursor compositions for such thermal deposition processes. Of particular interest are volatile organosilicon precursors containing appropriate ratios of silicon, nitrogen and carbon.

In addition, to be compatible with the next generation IC device manufacturing, PMD-liners need to be deposited at temperatures less than about 450° C., preferably about 400° C. For this application, low energy density plasmas would be acceptable. Further, etch stop and capping layers to be integrated with low k dielectrics and copper wiring need to be deposited at temperatures below about 400° C., preferably below about 350° C. These layers need to have high structural integrity, good barrier properties with respect to copper diffusion, and a dielectric constant significantly less than that of silicon nitride. For etch stop and capping layers application, PECVD is also acceptable. Again, volatile organosilicon precursors containing appropriate ratios of silicon, nitrogen and carbon are preferable.

Previously, we demonstrated that disilane precursors can offer high deposition rates at low temperatures. For example, silicon nitride films may be deposited at a rate of 26 Å/min by CVD at 450° C. using a mixture of hexaethylamidodisilane (HEADS) precursor and ammonia. Without being bound by theory, the high growth rate is attributed to the weak silicon-silicon bond in the disilane compound, which has a bond energy of 222 kJ/mol. In addition, it has been reported that higher temperatures induce lower deposition rates at the substrate because the reactant desorbs from the surface with the increase in temperature. Notably, disilane ($Si_2H_6$) and hexachlorodisilane (HCDS) ($Si_2Cl_6$), which have the weak Si—Si bond, also have been considered as promising precursors, however, they provide no source of carbon atoms. Further, chlorine may be incorporated into the fabricated chips, which could significantly reduce the chips long-term performance.

The art therefore has a continuing need for improved organosilicon precursors for forming silicon-containing films, such as low k silicon-containing thin films including silicon oxynitride, silicon nitride, silicon carbonitride and silicon oxycarbonitride.

SUMMARY OF THE INVENTION

The present invention relates generally to the formation of silicon-containing films in the manufacture of semiconductor devices, and more specifically to novel silicon precursors and methods for forming silicon-containing films, such as silicon-containing low k films and films comprising silicon carbonitride (Si—C—N), and silicon oxycarbonitride (Si—O—C—N), on a substrate using low temperature (T<550° C.) CVD processes.

The present invention in one aspect relates to a silicon compound selected from the group consisting of:
(A) compounds of the formula:

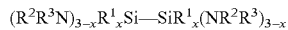

wherein:
R$^1$, R$^2$, and R$^3$ may be the same as or different from one another and each is independently selected from the group consisting of H, C$_1$-C$_5$ alkyl, C$_3$-C$_6$ cycloalkyl, aryl, arylalkyl; and
x is 1 or 2);
(B) compounds of the formula:

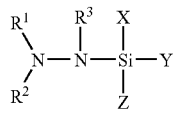

wherein R$^1$, R$^2$ and R$^3$ may be the same as or different from the other and each is independently selected from the group consisting of H, C$_1$-C$_5$ alkyl, C$_3$-C$_6$ cycloalkyl, aryl and arylalkyl; and
X, Y, and Z may be the same as or different from the other and each is independently selected from the group consisting of H, alkyl, alkylamino, dialkylamino and alkylhydrazido;
with the proviso that when R$^1$, R$^2$, X and Y are methyl groups and R$^3$ is hydrogen, Z cannot be hydrogen; and
(C) compounds of the formula:

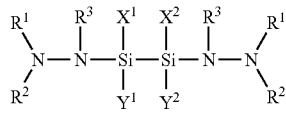

wherein R$^1$, R$^2$ and R$^3$ may be the same as or different from the other and each is independently selected from the group consisting of H, C$_1$-C$_5$ alkyl, C$_3$-C$_6$ cycloalkyl, aryl and arylalkyl; and
X$^1$, X$^2$, Y$^1$, Y$^2$, Z$^1$ and Z$^2$ may be the same as or different from the other and each is independently selected from the group consisting of H, alkyl, alkylamino, dialkylamino and alkylhydrazido.

Another aspect of the present invention relates to a method of forming a silicon-containing film on a substrate, comprising contacting a substrate under chemical vapor deposition conditions, at a temperature below 600° C., with a vapor of a silicon compound selected from the group consisting of:

(A) compounds of the formula:

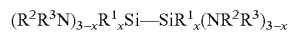

wherein:
R$^1$, R$^2$, and R$^3$ may be the same as or different from one another and each is independently selected from the group consisting of H, C$_1$-C$_5$ alkyl, C$_3$-C$_6$ cycloalkyl, aryl, arylalkyl; and
x is 1 or 2;
(B) compounds of the formula:

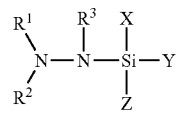

wherein R$^1$, R$^2$ and R$^3$ may be the same as or different from the other and each is independently selected from the group consisting of H, C$_1$-C$_5$ alkyl, C$_3$-C$_6$ cycloalkyl, aryl and arylalkyl; and
X, Y, and Z may be the same as or different from the other and each is independently selected from the group consisting of H, alkyl, alkylamino, dialkylamino and alkylhydrazido;
with the proviso that when R$^1$, R$^2$, X and Y are methyl groups and R$^3$ is hydrogen, Z cannot be hydrogen;
(C) compounds of the formula:

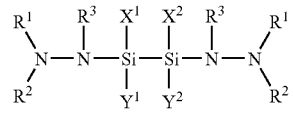

wherein R$^1$, R$^2$ and R$^3$ may be the same as or different from the other and each is independently selected from the group consisting of H, C$_1$-C$_5$ alkyl, C$_3$-C$_6$ cycloalkyl, aryl and arylalkyl; and
X$^1$, X$^2$, Y$^1$, Y$^2$, Z$^1$ and Z$^2$ may be the same as or different from the other and each is independently selected from the group consisting of H, alkyl, alkylamino, dialkylamino and alkylhydrazido; and
(D) compounds of the formula:

 (i)

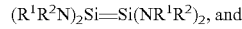 (ii)

(R$^1$R$^2$N)$_2$HSi—SiR$^3{}_n$H$_{3-n}$, (iii)

wherein R$^1$, R$^2$ and R$^3$ may be the same as or different from the other and each is independently selected from the group consisting of H, C$_1$-C$_4$ alkyl, amino, silyl groups (—SiH$_3$) and hydrocarbyl derivatives of silyl groups (e.g., —SiR$_3$); and 0≤n≤3.

Yet another aspect of the present invention relates to a method of making a silicon compound of the formula

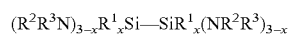

wherein:
R$^1$, R$^2$, and R$^3$ may be the same as or different from one another and each is independently selected from the group consisting of H, C$_1$-C$_5$ alkyl, C$_3$-C$_6$ cycloalkyl, aryl, arylalkyl; and
x is 1 or 2;
said method comprising reacting a disilane compound of the formula XR$^1$R$^2$Si—SiXR$^1$R$^2$ with a secondary amine (R$^2$R$^3$NH) and a tertiary amine (R$^1$R$^2$R$^3$N) compound, wherein X is selected from the group consisting of bromine, fluorine and chlorine, and R$^1$, R$^2$ and R$^3$ are as set out above, according to the following reaction:

XR$^1$R$^2$Si—SiXR$^1$R$^2$+R$^2$R$^3$NH+R$^1$R$^2$R$^3$N→(R$^2$R$^3$N)$_{3-x}$R$^1_x$Si—SiR$^1_x$(NR$^2$R$^3$)$_{3-x}$

Other aspects, features and embodiments of the invention will be more fully apparent from the ensuing disclosure and appended claims.

DETAILED DESCRIPTION OF THE INVENTION AND PREFERRED EMBODIMENTS THEREOF

Figure 1:
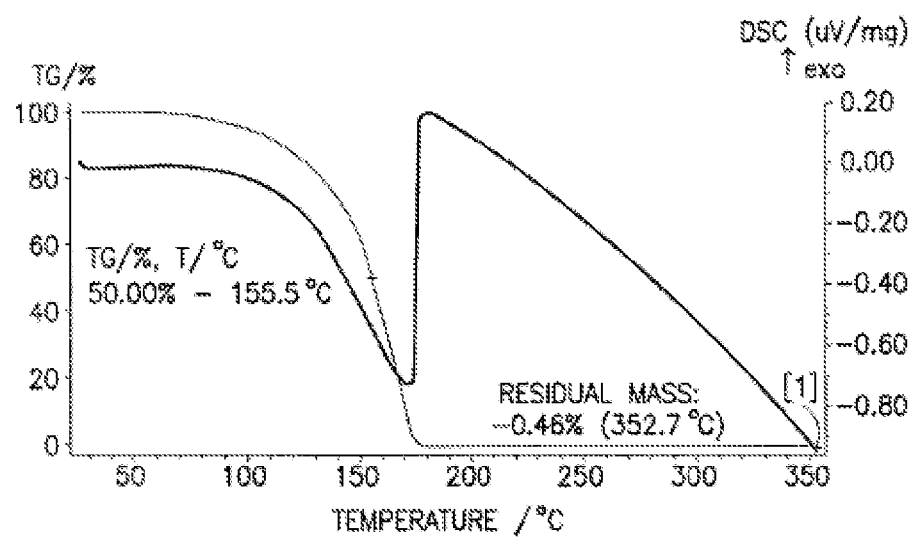
FIG. 1 is an STA plot for Me$_2$(NEt$_2$)Si—Si(NEt$_2$)Me$_2$ in Ar.

The present invention relates to novel silicon precursors for the CVD formation of silicon carbonitride and/or silicon oxycarbonitride films on substrates at low temperatures, and to corresponding processes for forming such films with such precursors.

In one aspect, the invention provides a compound of the formula:

(R$^2$R$^3$N)$_{3-x}$R$^1_x$Si—SiR$^1_x$(NR$^2$R$^3$)$_{3-x}$ (1)

wherein:
R$^1$, R$^2$, and R$^3$ may be the same as or different from one another and each is independently selected from the group consisting of H, C$_1$-C$_5$ alkyl, C$_3$-C$_6$ cycloalkyl, aryl, arylalkyl; and
x is 1 or 2.

The compounds of formula (1) are usefully employed for forming silicon-containing films by chemical vapor deposition, utilizing process conditions including a deposition temperature of less than 600° C., more preferably less than 550° C., and appertaining pressures, concentrations, flow rates and CVD techniques, as readily determinable within the skill of the art for a given application, based on the disclosure herein.

"Silicon-containing films" are defined herein means silicon nitride, silicon oxynitride, silicon carbonitride, silicon oxycarbonitride, low-k thin silicon-containing films, high-k gate silicate films and low temperature silicon epitaxial films.

Preferred compounds of formula (1) include Me$_2$(NEt$_2$)Si—Si(NEt$_2$)Me$_2$, Me$_2$(NEtMe)Si—Si(NEtMe)Me$_2$, and Me$_2$(NMe$_2$)Si—Si(NMe$_2$)Me$_2$.

Compounds of formula (1) are readily synthesized by reaction of disilane compounds of the formula R$^1_2$XSi—SiXR$^1_2$ with a secondary amine (R$^2$R$^3$NH) and a tertiary amine (R$^1$R$^2$R$^3$N) compound, wherein X is selected from the group consisting of bromine, fluorine and chlorine, and R$^1$, R$^2$ and R$^3$ are as set out above. For example, Me$_2$(NEt$_2$)Si—Si(NEt$_2$)Me$_2$ can be prepared according to the following reaction:

Me$_4$Si$_2$Cl$_2$+2NEt$_3$+2HNEt$_2$→Me$_4$Si$_2$(NEt$_2$)$_2$+2NEt$_3$.HCl as hereinafter more fully described in the examples herein.

The invention in another aspect relates to a group of halogen-free silanes or disilane derivatives that are substituted with at least one alkylhydrazine functional group and can be used as CVD precursors for deposition of silicon-containing thin films.

The silane derivatives of the present invention can be represented by the general formula:

(2)

wherein R$^1$, R$^2$ and R$^3$ may be the same as or different from the other and each is independently selected from the group consisting of H, C$_1$-C$_5$ alkyl, C$_3$-C$_6$ cycloalkyl, aryl and arylalkyl; and
X, Y, and Z may be the same as or different from the other and each is independently selected from the group consisting of H, alkyl, alkylamino, dialkylamino and alkylhydrazido (e.g., R$^1$R$^2$NNH—, wherein R$^1$ and R$^2$ are the same as described hereinabove);
with the proviso that when R$^1$, R$^2$, X and Y are methyl groups and R$^3$ is hydrogen, Z cannot be hydrogen.

The silane derivatives of the present invention can also be represented by the general formula:

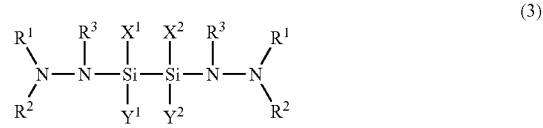

(3)

wherein R$^1$, R$^2$ and R$^3$ may be the same as or different from the other and each is independently selected from the group consisting of H, C$_1$-C$_5$ alkyl, C$_3$-C$_6$ cycloalkyl, aryl and arylalkyl; and
X$^1$, X$^2$, Y$^1$, Y$^2$, Z$^1$ and Z$^2$ may be the same as or different from the other and each is independently selected from the group consisting of H, alkyl, alkylamino, dialkylamino and alkylhydrazido.

Preferably, the disilane derivative compounds of the present invention are characterized by functional groups that are symmetrically distributed in relation to the Si—Si bond.

Compounds of formula (2) and (3) are readily synthesized by reaction of disilane compounds of the formula R$^1_2$XSi—SiXR$_2$ with an amine (R$^1$R$^2$R$^3$N) compound and a hydrazine compound (H$_2$NNR$_2$), wherein X is selected from the group consisting of bromine, fluorine and chlorine, and R$^1$, R$^2$ and R$^3$ are as set out above. For example, Me$_2$(Me$_2$NNH)Si—Si(NHNMe$_2$)Me$_2$ can be prepared according to the following reaction:

Me$_4$Si$_2$Cl$_2$+2NEt$_3$+2HNEt$_2$→Me$_4$Si$_2$(NEt$_2$)$_2$+2NEt$_3$.HCl as hereinafter more fully described in the examples herein.

The compounds of formulas (2) and (3) are usefully employed for forming silicon-containing films by chemical vapor deposition, utilizing process conditions including a deposition temperature of less than 600° C., more preferably less than 550° C., and appertaining pressures, concentrations, flow rates and CVD techniques, as readily determinable within the skill of the art for a given application, based on the disclosure herein.

Another class of silicon-containing precursors in accordance with the invention, which are amenable to CVD processes at low temperatures, such as in the range of from about 350° C. to about 550° C., for pre- and post-metal deposition of thin (e.g., 500 Angstroms to 1 micrometer thickness) dielectric films of silicon nitride or silicon oxynitride in semiconductor manufacturing, or otherwise for forming silicon nitride or silicon oxynitride ceramic thin films on different substrates, include the diaminosilylenes of formula (4) and their derivatives thereof, represented by formulae (5) and (6):

$$(R^1R^2N)_2Si: \qquad (4)$$

$$(R^1R^2N)_2Si=Si(NR^1R^2)_2 \qquad (5)$$

$$(R^1R^2N)_2HSi—SiR^3{}_nH_{3-n} \qquad (6)$$

wherein $R^1$, $R^2$ and $R^3$ may be the same as or different from the other and each is independently selected from the group consisting of H, $C_1$-$C_4$ alkyl, amino, silyl groups (—$SiH_3$) and hydrocarbyl derivatives of silyl groups (e.g., —$SiR_3$); and $0 \leq n \leq 3$.

Diamino-silylenes as represented by formula (4) are diradical species, some of which are not stable and easily form the derivatives as represented in formulae (5) and (6), while others are remarkably stable and can be readily delivered in their diradical form.

An exemplary stable silylene compound includes the following diaminosilylene:

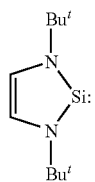

This diaminosilylene remains unchanged after boiling in toluene at 150° C. for four months. Thermal decomposition takes place at 220° C. The stability of this diaminosilylene is thought to result in part from aromatic stabilization (see, Denk, M., et al., *J. Am. Chem. Soc.*, 116, 2691-2692 (1994).

Diaminosilylenes represented by formula (4) can be synthesized according to the following mechanism (see, West, R., Denk, M., *Pure Appl. Chem.*, 68, 785-788 (1996)):

The compounds of formulae (5) and (6) can be made in accordance with the reaction scheme shown below:

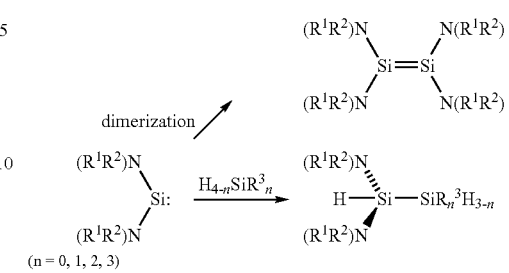

In accordance with teaching herein, the type of dielectric film produced by the corresponding CVD process can be tailored by choice of the specific silicon-containing precursor of formulae (1)-(6). For example, ammonia, oxygen or nitric oxide may be used as alternative single reactants to form the respective silicon nitride, silicon oxynitride, silicon carbonitride and/or silicon oxycarbonitride single component films, or a mixture of two or more of such reactants can be employed in the CVD process with selected one(s) of the formulae (1)-(6) precursors to form corresponding multicomponent films, or graded composition films. Alternatively, mono-, di- and trialkyl amines, of the formula $R^1R^2R^3N$ may be employed as reactants, wherein $R^1$, $R^2$ and $R^3$ may be the same as or different from the other and each is independently selected from the group consisting of H, and $C_1$-$C_4$ alkyl groups. In addition, inert carrier gases may be present in the precursor gas, including helium, argon and nitrogen.

In application, the silicon-containing precursor is reacted with a desired co-reactant in any suitable manner, e.g., in a single wafer CVD chamber, or in a furnace containing multiple wafers, utilizing process conditions including a deposition temperature of less than 600° C., more preferably less than <550° C., and appertaining pressures, concentrations, flow rates and CVD techniques, as readily determinable within the skill of the art for a given application, based on the disclosure herein. For example, when depositing sidewall spacers, PMD liners, or etch-stop and capping layers, temperatures of less than 550° C., less than 450° C., and less than 400° C., respectively, should be used. With respect to pressure, deposition pressures may range from about 1 Torr to about 80 Torr.

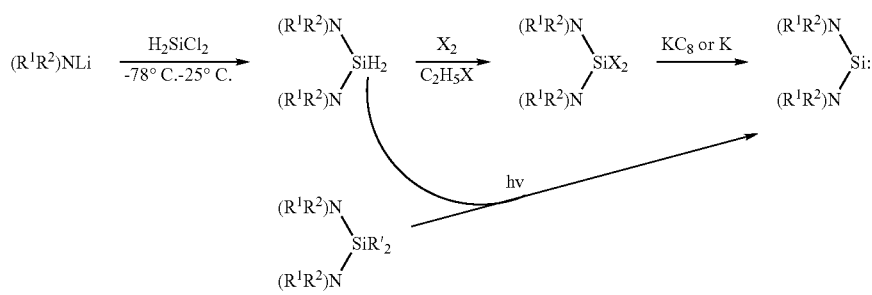

The features and advantages of the invention are more fully shown by the following illustrative and non-limiting examples.

Example 1

Synthesis of Me$_2$(NEt$_2$)Si—Si(NEt$_2$)Me$_2$

In a 1 L flask, 300 mL of hexanes and 350 mL (1.6 M, 560 mmol) of n-butyllithium in hexanes were mixed. To this solution, 41 g of HNEt$_2$ (560 mmol) was added at 0° C. White precipitate material was observed immediately. Upon completion of the addition, the reaction flask was allowed to warm to room temperature and stirred for an additional hour. Then, 50 g of Me$_4$Si$_2$Cl$_2$ (270 mmol) in 100 mL of diethyl ether was slowly added to the flask at room temperature. The mixture was stirred overnight and filtered at room temperature. The crude product, 59 g (227 mmol) 85% yield) was obtained after removal of the volatiles from the filtrate. The pure product was obtained by vacuum distillation (b.p. ~62° C. at 190 mTorr). $^1$H NMR(C$_6$D$_6$): 0.26 (s, 12H, —CH$_3$Si); 1.00 (t, 12H, —CH$_3$CH$_2$N); 2.83 (q, 8H, —CH$_3$CH$_2$N). $^{13}$C {$^1$H} NMR (C$_6$D$_6$): δ 0.33 (—CH$_3$Si); 16.2 (—NCH$_2$CH$_3$); 41.3 (—NCH$_2$CH$_3$). Mass spectrum: m/z 260 [M+]; 188 [M+-(—NEt$_2$)]; 130 [M+-(—SiMe$_2$(NEt$_2$)]. C$_{12}$H$_{32}$N$_2$Si$_2$. Found (theory) C, 54.98% (55.31%); H, 12.41% (12.38%); N, 10.66% (10.75%).

FIG. 1 shows that the STA data indicates that the T$_{50}$ value of Me$_2$(NEt$_2$)Si—Si(NEt$_2$)Me$_2$ is about 160° C., evidencing good volatility and transport properties for chemical vapor deposition.

Example 2

Synthesis of Me$_2$(Me$_2$NNH)Si—Si(NHNMe$_2$)Me$_2$

A 3 L flask was filled with a solution comprising 2.5 L of hexanes, 50 grams (267 mmol) of Me$_4$Si$_2$Cl$_2$, and 57 grams (561 mmol) of anhydrous NEt$_3$. 34 grams of H$_2$NNMe$_2$ (561 mmol), dissolved in 100 mL of diethyl ether, was slowly added to the flask at room temperature. White precipitate was observed during the addition of H$_2$NNMe$_2$ to the solution. Following completion of the addition, the mixture was stirred overnight, filtered, and all volatile materials were removed from the filtrate under vacuum. The crude yield was 86% (54 g, 230 mmol) Vacuum distillation was used to purify the end product, which has a boiling point of approximately 45° C. at 35 mTorr. $^1$HNMR (C$_6$D$_6$): δ 0.33 (s, 12H, —CH$_3$Si), 1.90 (br, 2H, —HN), 2.27 (s, 12H, —CH$_3$N). $^{13}$C{$^1$H} NMR (C$_6$D$_6$): δ –0.68 (—SiCH$_3$), 52.6 (—NCH$_3$). Mass spectrum: m/z 175 [M$^+$-(—HNNMe$_2$)], 132 [M$^+$-(—HNNMe$_2$)-(—NMe$_2$)], 116 [M$^+$-(—SiMe$_2$(HNNMe$_2$)]. C$_8$H$_{26}$N$_4$Si$_2$. Found (calculated) C, 40.81% (40.98%); H, 10.99% (11.18%); and N, 23.67% (23.89%).

Figure 2:
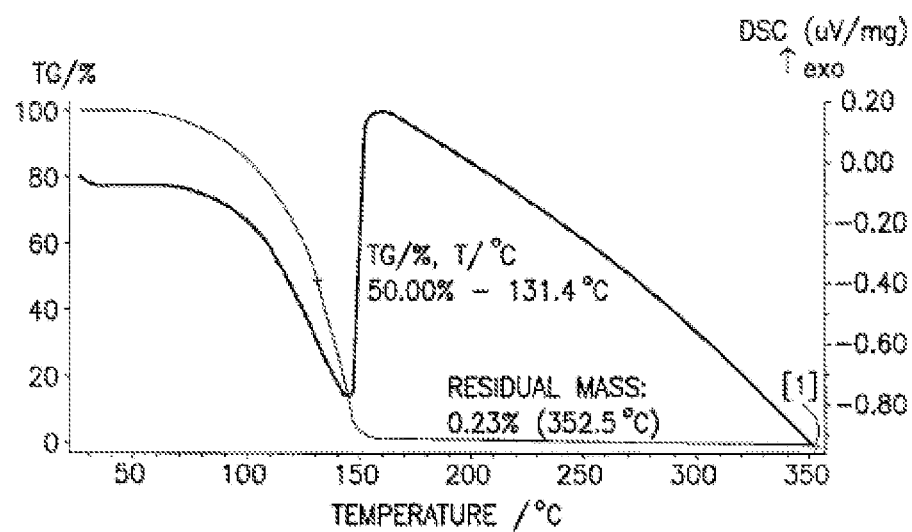
FIG. 2 is an STA plot for Me$_4$Si$_2$(NHNMe$_2$)$_2$ in Ar.

FIG. 2 shows the STA plot for Me$_4$Si$_2$(NHNMe$_2$)$_2$, which is a liquid at room temperature and can be transported in its vapor form completely with very little (<1%) residual material at about 350° C. The thermal stability of Me$_4$Si$_2$(HNNMe$_2$)$_2$ in solution at 100° C. was monitored by proton NMR study for 7 days, and no significant decomposition was detected.

Example 3

Silicon Carbonitride Deposition from Me$_4$Si$_2$(NHNMe$_2$)$_2$

A solution of the compound of Example 2, Me$_4$Si$_2$(NHNMe$_2$)$_2$, was prepared at a concentration of 0.40M in a hydrocarbon solvent. This solution was metered at 0.10 mL per minute (equivalent to about 2 sccm) with 10 sccm of He as a carrier gas and vaporized at 70° C. The vapor was mixed with 10 sccm of NH$_3$ in a showerhead device that was maintained at 100° C. and thereby dispersed over the surface of a Si(100) wafer heated to 550° C. The chamber pressure was maintained at 1 Torr during deposition. The film was deposited at a rate of 1.3 nm/minute.

Hydrocarbon solvents contemplated herein for use as precursor solvents include, but are not limited to, alkanes, alkenes, alkynes, cycloalkanes, aromatic compounds such as benzene and its derivatives thereof, alkanols and amines Chemical analysis of the film, using a combination of RBS (Rutherford Backscattering), HFS (Hydrogen Forward Scattering), and NRA (Nuclear Reaction Analysis) techniques, revealed that the film composition was 22.9% Si, 13.2% N, 33.1% C, 25.0% H and the index of refraction at 632 nm was 1.98.

While the invention has been described herein with reference to various specific embodiments, it will be appreciated that the invention is not thus limited, and extends to and encompasses various other modifications and embodiments, as will be appreciated by those ordinarily skilled in the art. Accordingly, the invention is intended to be broadly construed and interpreted, in accordance with the ensuing claims.

What is claimed is:

1. A composition comprising an inert carrier gas and a silicon compound of the formula

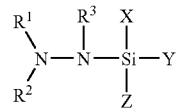

wherein R$^1$, R$^2$ and R$^3$ may be the same as or different from the other and each is independently selected from the group consisting of H, C$_1$-C$_5$ alkyl, C$_3$-C$_6$ cycloalkyl, aryl and arylalkyl; and X, Y, and Z may be the same as or different from the other and each is independently selected from the group consisting of H, alkyl, alkylamino, dialkylamino and alkylhydrazido;

with the proviso that when R$^1$, R$^2$, X and Y are methyl groups and R$^3$ is hydrogen, Z cannot be hydrogen, wherein said silicon compound is in a vapor form suitable for use under chemical vapor deposition conditions, and further comprising a co-reactant selected from among ammonia, nitric oxide, monoalkylamines, dialkylamines, and trialkyl amines, and mixtures of two or more thereof.

2. The composition of claim 1, wherein said inert gas is selected from among helium, argon and nitrogen.

3. The composition of claim 1, wherein pressure of said vapor is in a range of from about 1 Torr to about 80 Torr.

4. A composition comprising an inert carrier gas and a silicon compound of the formula

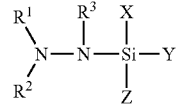

wherein $R^1$, $R^2$ and $R^3$ may be the same as or different from the other and each is independently selected from the group consisting of H, $C_1$-$C_5$ alkyl, $C_3$-$C_6$ cycloalkyl, aryl and arylalkyl; and each of X, Y and Z is alkylamino, and wherein said silicon compound is in a vapor form suitable for use under chemical vapor deposition conditions.

5. The composition of claim 4, further comprising a co-reactant.

6. The composition of claim 5, wherein the co-reactant is selected from among ammonia, oxygen, nitric oxide, monoalkylamines, dialkylamines, and trialkyl amines, and mixtures of two or more thereof.

7. The composition of claim 1, further comprising a solvent.

8. The composition of claim 7, wherein the solvent comprises a hydrocarbon solvent.

9. The composition of claim 7, wherein the hydrocarbon solvent is selected from the group consisting of alkanes, alkenes, alkynes, cycloalkanes, aromatic compounds, benzene, benzene derivatives, alkanols and amines.

10. The composition of claim 7, wherein the solvent comprises an alkane solvent.

11. The composition of claim 1, wherein $R^1$, $R^2$ and $R^3$ are the same as one another.

12. The composition of claim 1, wherein $R^1$, $R^2$ and $R^3$ are different from one another.

13. The composition of claim 1, wherein $R^1$, $R^2$ and $R^3$ are each hydrogen.

14. The composition of claim 1, wherein $R^1$ and $R^2$ are each selected from $C_1$-$C_5$ alkyl and $R^3$ is hydrogen.

15. The composition of claim 1, wherein $R^1$ and $R^2$ are each selected from $C_3$-$C_6$ cycloalkyl, aryl and arylalkyl.

16. The composition of claim 1, wherein each of X, Y and Z is alkyl.

17. The composition of claim 1, wherein each of X, Y and Z is dialkylamino.

18. The composition of claim 1, wherein each of X, Y and Z is alkylhydrazido.

19. The composition of claim 4, further comprising a hydrocarbon solvent.

20. The composition of claim 19, wherein the hydrocarbon solvent comprises an alkane solvent.

* * * * *

UNITED STATES PATENT AND TRADEMARK OFFICE
CERTIFICATE OF CORRECTION

PATENT NO. : 8,802,882 B2  Page 1 of 1
APPLICATION NO. : 12/862739
DATED : August 12, 2014
INVENTOR(S) : Ziyun Wang It is certified that error appears in the above-identified patent and that said Letters Patent is hereby corrected as shown below:

In the Specification

Column 6, lines 49-50: "$R^1_2XSi\text{—}SiXR_2$" should be -- $R^1_2XSi\text{—}SiXR^1_2$ --.

Column 6, line 51: "$H_2NNR_2$" should be -- $H_2NNR^1_2$ --.

Column 6, lines 57-58: "$Me_4Si_2Cl_2 + 2NEt_3 + 2HNEt_2 \rightarrow Me_4Si_2(Net_2)_2 + 2NEt_3.HCl$" should be -- $Me_4Si_2Cl_2 + 2\ NEt_3 + 2\ H_2NNMe_2 \rightarrow Me_4Si_2(NHNMe_2)_2 + 2\ NEt_3.HCl$ --.

Column 9, line 44: "230 mmol) Vacuum" should be -- 230 mmol). Vacuum --.

Signed and Sealed this
Twenty-sixth Day of May, 2015

Michelle K. Lee
*Director of the United States Patent and Trademark Office*